US011478410B2

(12) United States Patent
Kikuchi et al.

(10) Patent No.: US 11,478,410 B2
(45) Date of Patent: Oct. 25, 2022

(54) LIQUID COSMETIC WITH AGAR SHELL CAPSULE

(71) Applicant: LVMH RECHERCHE, Saint Jean de Braye (FR)

(72) Inventors: Masahiro Kikuchi, Tokyo (JP); Mai Ozawa, Tokyo (JP); Takayoshi Sakoda, Tokyo (JP)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 16/755,818

(22) PCT Filed: Dec. 18, 2017

(86) PCT No.: PCT/EP2017/083323
§ 371 (c)(1),
(2) Date: Apr. 13, 2020

(87) PCT Pub. No.: WO2019/120473
PCT Pub. Date: Jun. 27, 2019

(65) Prior Publication Data
US 2021/0186835 A1   Jun. 24, 2021

(51) Int. Cl.
| | | |
|---|---|---|
| *A61K 8/34* | (2006.01) | |
| *A61K 8/03* | (2006.01) | |
| *A61K 8/04* | (2006.01) | |
| *A61K 8/11* | (2006.01) | |
| *A61K 8/37* | (2006.01) | |
| *A61K 8/73* | (2006.01) | |
| *A61K 8/81* | (2006.01) | |
| *A61K 8/92* | (2006.01) | |
| *A61K 8/9717* | (2017.01) | |
| *A61K 8/9728* | (2017.01) | |
| *A61Q 19/00* | (2006.01) | |

(52) U.S. Cl.
CPC ............... *A61K 8/345* (2013.01); *A61K 8/03* (2013.01); *A61K 8/04* (2013.01); *A61K 8/044* (2013.01); *A61K 8/11* (2013.01); *A61K 8/375* (2013.01); *A61K 8/73* (2013.01); *A61K 8/733* (2013.01); *A61K 8/735* (2013.01); *A61K 8/8141* (2013.01); *A61K 8/8152* (2013.01); *A61K 8/92* (2013.01); *A61K 8/9717* (2017.08); *A61K 8/9728* (2017.08); *A61Q 19/00* (2013.01); *A61Q 19/007* (2013.01); *A61K 2800/262* (2013.01); *A61K 2800/43* (2013.01); *A61K 2800/594* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 2003/0190336 A1* | 10/2003 | Adams | ................ | A61K 8/0241 |
| | | | | 424/401 |
| 2011/0002865 A1* | 1/2011 | Fournial | .............. | A61K 8/0212 |
| | | | | 514/354 |

FOREIGN PATENT DOCUMENTS

| | | |
|---|---|---|
| EP | 1172083 | 1/2002 |
| FR | 2660212 | 10/1991 |
| JP | H03284607 | 12/1991 |
| JP | H05310529 | 11/1993 |
| JP | 2000502677 | 3/2000 |
| JP | 2003238351 | 8/2003 |
| JP | 2013194033 | 9/2013 |
| WO | 9723194 | 7/1997 |

OTHER PUBLICATIONS

FR2660212 machine-assisted English translation (Year: 1991).*
FR2660212 claims (English translated) (Year: 1991).*
"Campaign for Safe Cosmetics" (internet article obtained from the website https://www.safecosmetics.org/get-the-facts/chemicals-of-concern/fragrance/) (date unknown).*
Machine-assisted English translation for JP2003-238351 (Year: 2003).*
Derwent English translation for JP2003-238351 (Year: 2003).*
International Search Report and Written Opinion issued for International Patent Application No. PCT/EP2017/083323, dated Aug. 3, 2018, 14 pages.
Database GNPD [Online] Mintel; Feb. 2008, Kao: "Moist Capsule Essence," XP002783274, Database accession No. 855721 (2 pages).
Database WPI, Week 200376, Sep. 1, 2003, Thomson Scientific, London, GB; AN 2003-808161, XP002783275 (2 pages).
"Capsule for Cosmetics and Quasi-Drugs," Aug. 20, 2016, pp. 1-2, XP055494747, Retrieved from the Internet: URL: https://web.archive.org/web/20160820154015/http://www.fujicapsule.com/english/softcapsule/selfcut.html [retrieved on Jul. 24, 2018], Advantages of soft agar capsule & Aqua Julie.
Database GNPD [Online] Mintel; Jan. 2016, Bielenda: "Day/Night Facial Serum," XP002783276, Database accession No. 3671599 (5 pages).

(Continued)

*Primary Examiner* — Sin J Lee
(74) *Attorney, Agent, or Firm* — Hamre, Schumann, Mueller & Larson, P.C.

(57) ABSTRACT

The invention provides a liquid cosmetic that contains capsule in an aqueous medium, wherein the capsule comprises agar shell encapsulating an oil component, and the aqueous medium comprises a low molecular polyol and one selected from the group consisting of a (meth)acrylic polymer and a polysaccharide.

4 Claims, No Drawings

(56) References Cited

OTHER PUBLICATIONS

Database GNPD [Online] Mintel; Apr. 2016, Carver Korea: "Essence," XP002783277, Database accession No. 3825977 (6 pages).
Database GNPD [Online] Mintel; Aug. 2017, Prostemics: "Skin Glow Solution 2," XP002783278, Database accession No. 5013989 (2 pages).
Database GNPD [Online] Mintel; Nov. 2017, Johnson & Johnson: "Capsule in Serum," XP002783279, Database accession No. 5269601 (5 pages).

* cited by examiner

LIQUID COSMETIC WITH AGAR SHELL CAPSULE

BACKGROUND OF THE INVENTION

Field of the Invention

The present invention relates to a liquid cosmetic.

Related Background Art

Cosmetics in the form of cosmetic lotion, emulsion or essences have traditionally been used to help moisturize the skin and remedy problems such as roughened skin. Some recent types of cosmetic materials include dispersed capsules containing beautifying ingredients or gel particles. A cosmetic containing hydrogel particles encapsulating a brightness agent powder is disclosed in PTL 1. The disclosed hydrogel particles are dispersed in a gel which suppresses their settling or floating.

CITATION LIST

Patent Literature

[PTL 1] Japanese Unexamined Patent Application Publication No. 2013-194033

SUMMARY OF THE INVENTION

A conventional cosmetic having capsules dispersed in an aqueous medium usually becomes turbid over time, which not only adversely affects the appearance of the cosmetic but also impairs its homogeneity, and when it is subsequently applied to the skin it fails to adequately exhibit its original moisturizing or emollient effect.

The present inventors have found that the capsules of conventional capsule-containing aqueous cosmetics may become damaged by impact or progressive alteration, causing the contents of the capsules to leak out. Furthermore, when components such as low molecular polyols are present in the aqueous medium, they cause the capsule contents (which include oil components) to be extracted into the aqueous medium. The cosmetic tends to become turbid as a result.

It is an object of the present invention to provide a liquid cosmetic comprising capsules in an aqueous medium (a capsule-containing liquid cosmetic), which has less turbidity produced over time while maintaining its original skin care effect over extended periods.

Specifically, the invention provides a liquid cosmetic containing a capsule in an aqueous medium, wherein the capsule comprises agar shell encapsulating an oil component, and the aqueous medium comprises a low molecular polyol and at least one polymer selected from the group consisting of a (meth)acrylic polymer and a polysaccharide.

The liquid cosmetic of the invention uses an agar shell for the capsule in combination with a low molecular polyol in an aqueous medium, and with further addition of one selected from the group consisting of a (meth)acrylic polymer and a polysaccharide. This results in a surprising reduction in damage caused by impact, as well as less leakage of the oil component from the capsules due to the low molecular polyol and therefore lower progressive turbidity (particularly turbidity at low temperatures) caused by the oil components. Moreover, since the cosmetic maintains high stability over time, its original effect is maintained over long periods.

The liquid cosmetic also includes agar in the capsule shell, and the moisture-retaining property of the agar itself functions together with the low molecular polyol capable of functioning as the humectant, thus increasing and also helping to prolong the skin-moisturizing effect. Moreover, the oil component encapsulated in the capsules can provide a moisturizing, nourishing and emollient effect on the skin.

The oil component may also include a colorant, as including a colorant in the capsule enhances the aesthetic quality of the cosmetic. However, in a conventional capsule-containing aqueous cosmetic, added colorants tend to leak out into the aqueous medium together with the capsule contents, and because this tends to make the instability of the product more conspicuous rather than enhancing the aesthetic quality (which is the purpose of adding the colorant to the capsules), it has not been feasible to add colorants to such capsules. With the liquid cosmetic of the invention, however, the colorant remains more stably in the capsules for prolonged periods, and the transparency of the agar forming the outer shell allows the original effect of the cosmetic to be exhibited while maintaining high aesthetic quality.

The specific gravity of the capsules may be different from that of the aqueous medium. When filled into a container, the capsules stay either at upper side or at lower side of the aqueous medium. This produces two visible separated layers in the liquid cosmetic, a layer comprising the capsules and a layer comprising the aqueous medium, so that an excellent aesthetic quality is provided in addition to the functions mentioned above.

In a liquid cosmetic in which the specific gravity of the capsules is different from the specific gravity of the aqueous medium, the capsules housed in the container tend to separate out from the aqueous medium. However, shaking the container allows the capsules to be kept in a dispersed state in the aqueous medium until the cosmetic is applied.

Since shaking this type of liquid cosmetic allows the dispersed state of the capsules in the aqueous medium to be maintained for a certain period of time without immediate re-separation between the capsule-containing layer and the aqueous medium-containing layer, the liquid cosmetic can be more easily used with the capsules in the dispersed state, and the function of the cosmetic can be more easily and reliably exhibited.

According to the invention it is possible to provide a liquid cosmetic comprising capsules in an aqueous medium which exhibits less turbidity over time while maintaining its original cosmetic effect over extended periods.

DESCRIPTION OF EMBODIMENTS

Embodiments of the invention will now be described. However, the present invention is not limited to the embodiments described below.

The liquid cosmetic (capsule-containing liquid cosmetic) according to a preferred embodiment comprises a capsule with oil component-encapsulating agar shell in an aqueous medium.

Here, a "capsule" means a particle composed of an agar shell and contents, the contents being encapsulated in the outer shell. The capsule shapes may be spherical or spindle-shaped, for example.

The term "agar shell" refers to an outer shell containing agar, and it may consist entirely of agar or alternatively may partly contain components other than agar. Such other components may be alginic acid salts, carrageenan and the like, which include inorganic salts such as sodium salts, potassium salts, ammonium salts and lithium salts. Because agar easily retains moisture from skin, the presence of agar in the capsule outer shells increases the moisturizing effect of the liquid cosmetic on skin while also lengthening the duration of the moisturizing effect. In order to improve its durability, the outer shell preferably consists only of agar.

The oil component in the capsule contains: (1) an oil; (2) an oil soluble or dispersible component; and (3) components combining these. Provided that it includes (1) to (3), the oil component may contain other components in amounts that do not impede the effects of the invention.

Oils include hydrocarbon oils, fat oils, waxes, hydrogenated oils, ester oils, fatty acids, silicone oils and fluorine-based oils. By encapsulating an oil component in the capsules, the liquid cosmetic will be able to provide a high nourishing effect for skin.

Hydrocarbon oils include liquid paraffin, light liquid isoparaffin, dodecane, isododecane, tetradecane, isotetradecane, hexadecane, isohexadecane, squalane, vegetable squalane, vaseline, polyisobutylene, polybutene and other oils.

Fat oils include Japan wax, olive oil, castor oil, mink oil, macadamia nut oil, camellia oil, rose hip oil and avocado oil.

Waxes include beeswax, lanolin, carnauba wax, candelilla wax and spermaceti wax.

Ester oils include jojoba oil, cetyl isooctanoate, glyceryl tri(caprylate/caprate), isopropyl myristate, isopropyl palmitate, octyldodecyl myristate, glyceryl trioctanoate (triethylhexanoin), polyglyceryl diisostearate, diglyceryl triisostearate, glyceryl tribehenate, diisostearyl malate, neopentylglycol dioctanoate and cholesterol fatty acid esters.

Fatty acids include lauric acid, myristic acid, palmitic acid, stearic acid, behenic acid, oleic acid and other fatty acids.

Silicone oils include polydimethylsiloxane (dimethicone), polymethylphenylsiloxane (diphenyldimethicone), phenyltrimethicone, diphenylsiloxyphenyltrimethicone, amino-modifiedsilicone, epoxy-modifiedsilicone, carboxy-modified silicone, polyether-modified silicone, alkyl-modified silicone and fluorine-modified silicone.

Fluorine-based oils include perfluoropolyethers, perfluorodecalin and perfluorooctane.

Oil soluble or dispersible components may be colorants, active ingredients or other adjuvants such as antioxidants.

The oil content may be 0 to 100 mass %, based on the total weight of the oil component (the capsule contents), and preferably is 50 to 100 mass %. When the oil content is 0 mass %, an oil-soluble or oil-dispersible component would be included.

Colorants that can be included in the oil component include oil-soluble colorants and oil-dispersible colorants. When using an oil-soluble colorant, the colorant may be one that is either soluble in oils exclusively or soluble in both oils and alcohols. An example of a colorant that dissolves exclusively in oil is marigold colorant (marigold pigment). Blue #403 (Sudan Blue B) is an example of a colorant that dissolves in both oils and alcohols. When using an oil-dispersible colorant, the colorant may be one that is dispersible in oils and may be categorized as a water-soluble colorant. Red #103-(1), yellow #4 and blue #1 are examples of oil-dispersible colorants.

The colorant content may be 0 to 20 mass %, for example, based on the total weight of the oil component (the capsule contents).

Examples of the active ingredients added to the oil component include ones having beautifying effects on the skin, including effects against skin roughening and wrinkles. Such examples of active ingredients include the fat-soluble vitamins, and specifically vitamin A compounds such as retinol, retinol palmitate and retinol acetate, vitamin D compounds such as ergocalciferol and cholecalciferol, and vitamin E compounds such as tocopherol and tocotrienol. Active ingredients can also function as colorants, as is the case with carotenoids such as astaxanthin, lycopene and fucoxanthin.

The active ingredient content may be 0 to 100 mass %, for example, based on the total weight of the oil component (the capsule contents), and is preferably 0 to 50 mass %.

The capsules have a mean particle size of preferably 0.1 mm or greater, more preferably 0.3 mm or greater and even more preferably 0.5 mm or greater, and preferably no greater than 8 mm, more preferably no greater than 6 mm and even more preferably no greater than 4 mm. This will ensure that the shell thickness is sufficient to allow the oil component to be completely encapsulated, while providing the capsules with an excellent appearance. The mean particle size of the capsules can be calculated by imaging regions of the liquid cosmetic including at least 10 particles, and calculating the mean size from those images.

The thicknesses of the outer shells of the capsules are preferably from 2 to 90% of the mean particle size of the capsules, the percentage being more preferably 5 to 80%. Restricting the outer shell thicknesses to within this range can more effectively prevent leakage of the oil component inside them and reduce damage by impact.

The specific gravity of the capsules may be different from that of the aqueous medium. That is, the specific gravity of the capsules may be either greater than or less than that of the aqueous medium. This will provide the liquid cosmetic with a two-layer appearance as the capsules settle or float in the aqueous medium when the liquid cosmetic is allowed to stand. The specific gravity of the capsules is preferably less than that of the aqueous medium.

When the specific gravity of the capsules differs from the specific gravity of the aqueous medium, the capsules housed in the container are in a state of separation from the aqueous medium, but shaking the container by hand allows the capsules to be kept in a dispersed state in the aqueous medium until the cosmetic is applied. For example, manually shaking a 10 to 500 mL-volume container up and down 3 to 5 times allows the dispersed state of the capsules in the aqueous medium to be maintained for 1 minute to 12 hours. Capsule dispersion of between 1 minute to 12 hours is sufficient time for the cosmetic to be applied to the skin or the like. The specific gravity of the capsules is preferably within ±20% of the specific gravity of the aqueous medium, with a smaller difference between them being preferred for a longer dispersed period.

For an even higher moisturizing effect exhibited by the liquid cosmetic, the capsule content is preferably 5 mass % or greater, more preferably 10 mass % or greater and even more preferably 15 mass % or greater, based on the total liquid cosmetic mass. The capsule content is also preferably no greater than 65 mass %, more preferably no greater than 60 mass % and even more preferably no greater than 55 mass %, and preferable from 20 mass % to 50 mass %, based on the total liquid cosmetic mass, in order to more effectively minimize disintegration of the capsule agar shells and to obtain a liquid cosmetic with an excellent appearance.

The aqueous medium of this embodiment contains water, one selected from the group consisting of a (meth)acrylic polymer and a polysaccharide, and a low molecular polyol. Note that the term "(meth)acrylic" refers to acrylic or methacrylic, and the same is also true of other similar structures.

The water used may be distilled water, purified water, hot spring water, deep water, or plant-derived steam distilled water such as lavender water, rose water or orange flower water. The water content may be from 20 mass %, 23 mass % or 25 mass %, to 80 mass %, 75 mass % or 70 mass %, based on the total liquid cosmetic mass.

The (meth)acrylic polymer may be an alkyl (meth)acrylate copolymer, (meth)acrylic acid-alkyl (meth)acrylate copolymer or its salt, or a derivative or salt of a (meth) acrylic acid-alkyl (meth)acrylate copolymer. The copolymers mentioned also include their crosslinked forms.

Some of the available copolymers include the alkyl acrylate copolymer: ACULYN 33 (Rohm & Haas); the acrylic acid-alkyl methacrylate copolymers (also crosslinked): PEMULEN TR-1, PEMULEN TR-2, CARBOPOL ETD2020, CARBOPOL 1382, CARBOPOL 1342, ULTREZ 20 polymer and ULTREZ 21 polymer (Lubrizol Advanced Materials); AQUPEC HV-501ER, AQUPEC SER W-300C and AQUPEC SER W-150C (Sumitomo Seika Chemicals Co., Ltd.); and (meth)acrylic acid-alkyl (meth) acrylate copolymer derivatives or their salts, such as polyoxyethylenealkyl ether ester copolymers of acrylic acid-methacrylic acid-alkyl acrylate-alkyl methacrylate-methacrylic acid, having a polyoxyethylenealkyl ether ester-bonded to a (meth)acrylic acid-alkyl (meth)acrylate copolymer (such as alkyl acrylate-alkyl methacrylate-polyoxyethylene(20) stearyl ether copolymer (ACULYN 22, Rohm & Haas)).

Preferred (meth)acrylic polymers are Acrylate/C10-30 Alkyl Acrylate and Acrylate/C10-30 Alkyl Acrylate Crosspolymer. Specifically, preferred copolymers are any one or more selected from the group consisting of (a) a copolymer comprising an alkyl (meth)acrylate ester with a C10 to 30 alkyl group and (meth)acrylic acid as a monomer unit, (b) a crosslinked copolymer comprising an alkyl (meth) acrylate ester with a C10 to 30 alkyl group, (meth)acrylic acid and pentaerythritol allyl ether as a monomer unit, (c) a crosslinked copolymer comprising an alkyl (meth)acrylate ester with a C10 to 30 alkyl group, (meth)acrylic acid and sucrose allyl ether as a monomer unit, and (d) a crosslinked copolymer comprising an alkyl (meth)acrylate ester with a C10 to 30 alkyl group, (meth)acrylic acid, pentaerythritol allyl ether and sucrose allyl ether as a monomer unit. PEMULEN TR-1, PEMULEN TR-2, CARBOPOL ETD2020, CARBOPOL 1342, CARBOPOL 1382, ULTREZ 20 polymer, ULTREZ 21 polymer, AQUPEC SER W-300C and AQUPEC SER W-150C mentioned above are examples of such copolymers.

The (meth)acrylic polymer content is preferably 0.005 mass % or greater, more preferably 0.007 mass % or greater and even more preferably 0.01 mass % or greater, and preferably no greater than 0.20 mass %, more preferably no greater than 0.10 mass % and even more preferably no greater than 0.05 mass %, based on the total liquid cosmetic mass.

The polysaccharide may be xanthan gum, hyaluronic acid, sodium hyaluronate or acetylated hyaluronic acid, for example, and it may be organically derived. Organically derived polysaccharides include *Tremella fuciformis* polysaccharide (extracted from *Tremella fuciformis*), having glucuronic acid, mannose and xylose as constituent monosaccharides (for example, Tremoist TP, trade name of Nippon Seika Co., Ltd.).

The polysaccharide content is preferably 0.003 mass % or greater, more preferably 0.005 mass % or greater and even more preferably 0.007 mass % or greater, and preferably no greater than 0.5 mass %, more preferably no greater than 0.3 mass % and even more preferably no greater than 0.2 mass %, based on the total liquid cosmetic mass. This range can further reduce disintegration of the agar shells or leakage of the oil component from the capsules.

When the liquid cosmetic comprises one selected from the group consisting of a (meth)acrylic polymer and a polysaccharide, there will be less disintegration of the agar shells and leakage or dispersion of the oil component into the aqueous medium, and therefore lower turbidity of the liquid cosmetic. Since (meth)acrylic polymers and polysaccharides will have effects of increasing the viscosity of the aqueous medium, this will allow the dispersed state of the capsules in the aqueous medium to be maintained for a certain amount of time when the liquid cosmetic is shaken after the capsules have floated or settled.

A combination of a (meth)acrylic polymer and polysaccharide may also be used, when the oil component encapsulated in the capsules includes an oil-soluble colorant, either soluble in oils exclusively or soluble in both oils and alcohols (alcohol-soluble colorant).

The "low molecular polyol" is defined as one whose molecular weight (Mw) is not greater than 8,000, preferably not greater than 1,500 and more preferably not greater than 500. The low molecular polyol may be a glycol such as 1,3-propanediol, propylene glycol, butylene glycol, pentylene glycol, dipropylene glycol or polyethylene glycol such as PEG-8, a glycerol such as glycerin, diglycerin or polyglycerin, or a sugar alcohol such as sorbitol. A single type of low molecular polyol may be used, or two or more different types may be used in combination.

The low molecular polyol content is preferably 3 mass % or greater, more preferably 5 mass % or greater and even more preferably 7 mass % or greater based on the total liquid cosmetic mass. This will allow the moisturizing effect of the liquid cosmetic to be further increased, and will prevent decay of the liquid cosmetic so that it can be stored for prolonged periods. The low molecular polyol content is preferably no greater than 30 mass %, more preferably no greater than 25 mass % and even more preferably no greater than 20 mass %, based on the total liquid cosmetic mass.

In addition to the various materials mentioned above, the liquid cosmetic of the present embodiment may also contain monohydric alcohols, pH regulators, electrolytes, perfumes, emulsifying agents, solubilizing agents, antioxidants, discoloration preventers and stabilizers as appropriate.

An electrolyte can stabilize the liquid cosmetic while also exhibiting beautifying effects, including a moisturizing effect, or whitening and anti-inflammatory effects for skin, and examples of electrolytes include edetic acid, citric acid, lactic acid, glycolic acid, succinic acid, tartaric acid, malic acid, ascorbic acid and glycyrrhizinic acid, as well as their salts. A single electrolyte may be used alone, or two or more may be used in combination.

A monohydric alcohol serves as an antiseptic agent, and phenoxyethanol, for example, may be used. When a pH regulator is used, it may be sodium hydroxide, for example.

The viscosity of the liquid cosmetic may be 20 mPas, 30 mPas, 50 mPas or higher, and up to 1,200 mPas, 800 mPas or 600 mPas, as measured using a rotational rheometer Rheolab QC in following conditions (spindle: CC27; revolution speed: 200 rpm; measuring time: 3 min).

The liquid cosmetic can be prepared by mixing water and a monohydric alcohol as necessary, adding to the mixture a (meth)acrylic polymer and/or polysaccharide and allowing it to swell, and then adding a pH neutralizer if necessary, for neutralization, after which other materials may then be added to and mixed with it.

The liquid cosmetics of each of the embodiments described above are particularly suitable for use as lotions (cosmetic water) and essences.

EXAMPLES

The invention will now be illustrated by examples, with the understanding that the invention is not meant to be limited to these examples.

Examples 1 to 4, Comparative Examples 1 to 3

Liquid cosmetics containing capsules in aqueous media were prepared with the compositions listed in Table 1. First, a (meth)acrylic polymer (column "b") and/or a polysaccharide (column "c") were added to an aqueous solution of water and phenoxyethanol (column "a"), and the (meth)acrylic polymer and/or polysaccharide were allowed to swell. After then adding aqueous sodium hydroxide or water (column "d"), and further adding a low molecular polyol (column "e") and oil component-encapsulating agar shell capsules (column "f"), the components were mixed to form a liquid cosmetic. The component contents (mass %) were as shown in Table 1.

Samples in which no turbidity of the medium and no leakage of oil components from the capsules was observed were evaluated as "A", those that exhibited turbidity were evaluated as "B", and those that had leakage of oil components were evaluated as "C". The results are shown in Table 1.

<Organoleptic Evaluation>

The moisturizing effects of the liquid cosmetics of Examples 1 to 4 and Comparative Examples 1 to 3 were evaluated in a single-use test on skin, by an expert cosmetic evaluation panel from an organization to which the present inventors belong, the evaluation being made on the following scale. The results are shown in Table 1.

A: Strong effect

B: Moderate effect

C: No effect

<Maintenance of the Dispersed State>

In the liquid cosmetics of Examples 1 to 4, the capsules separated so as to be present in the upper layer of the aqueous medium. It was discovered that, when the liquid cosmetics of Examples 1 to 4 were placed in a 30 mL container and shaken up-and-down three times by hand, the capsules could be kept in a dispersed state in the aqueous medium for between 1 to 300 minutes in any of the examples. This time was sufficient for the cosmetic to be applied to the skin or the like.

TABLE 1

| | | Example 1 | Example 2 | Example 3 | Example 4 | Comp. Ex. 1 | Comp. Ex. 2 | Comp. Ex. 3 |
|---|---|---|---|---|---|---|---|---|
| a | Water | 29.476 | 34.48 | 29.376 | 29.376 | 49.5 | 39.5 | 39.5 |
| | Phenoxyethanol | 0.5 | 0.5 | 0.5 | 0.5 | 0.5 | 0.5 | 0.5 |
| b ((Meth)acrylic polymer) | Alkyl acrylate/methacrylate copolymer (PEMULEN TR-2) | 0.02 | — | 0.02 | 0.02 | — | — | — |
| c (Polysaccharide) | Sodium hyaluronate (BASHYAL POUDRE) | — | — | 0.1 | 0.1 | — | — | — |
| | Tremella fuciformis polysaccharide (Tremoist TP) | — | 0.02 | — | — | — | — | — |
| d | Water | 5 | 5 | 5 | 5 | — | — | — |
| | Sodium hydroxide | 0.004 | — | 0.004 | 0.004 | — | — | — |
| e (Low-molecular polyol) | 1,3-Butyleneglycol | 6 | 10 | 6 | 6 | — | — | — |
| | Glycerin | 8 | — | 8 | 8 | — | 10 | — |
| | Pentyleneglycol | 1 | — | 1 | 1 | — | — | 10 |
| f (Agar shell capsules encapsulating an oil component) | Capsule 1 [glyceryl tri(caprylate/caprate), colorant (marigold colorant)] | 50 | — | — | 50 | — | — | — |
| | Capsule 2 [glyceryl tri(caprylate/caprate), colorant (Blue #403)] | — | 50 | 50 | — | 50 | 50 | 50 |
| Stability evaluation | 50° C. × 1 month | A | A | A | A | A | A | A |
| | −18° C. × 1 week | A | A | A | A | C | C | C |
| Organoleptic evaluation | Moisturizing effect | A | A | A | A | C | B | B |

<Stability Evaluation>
(1) One Month at 50° C.

Each cosmetic was filled into a transparent container and sealed with a cap, and then stored for 1 month at 50° C. After the storage period, each cosmetic was observed for the presence of any turbidity in the medium or leakage of oil components from the capsules. Samples in which no turbidity of the medium and no leakage of oil components from the capsules was observed were evaluated as "A", those that exhibited turbidity were evaluated as "B", and those that had leakage of oil components were evaluated as "C". The results are shown in Table 1.
(2) Freezing Test at −18° C.

Each cosmetic was filled into a transparent container and sealed with a cap, and then stored for 1 week at −18° C.

The invention claimed is:

1. A liquid cosmetic containing a capsule in an aqueous medium, wherein
   a shell of the capsule consists of agar and encapsulates an oil component, and
   the aqueous medium comprises a low molecular polyol and at least one polymer selected from the group consisting of an alkyl (meth)acrylate copolymer, optionally in crosslinked form, a (meth)acrylic acid-alkyl (meth)acrylate copolymer or its salt, optionally in crosslinked form, and a polysaccharide, a content of the low molecular polyol being 7 mass % or greater based on a total liquid cosmetic mass, and
   wherein the capsule separates out from the aqueous medium when housed in a container, and shaking the container allows the capsule to be in a dispersed state in the aqueous medium until the cosmetic is applied.

2. The liquid cosmetic according to claim 1, wherein the oil component contains a colorant.

3. The liquid cosmetic according to claim 1, wherein the capsule has a different specific gravity from the aqueous medium.

4. A method for hydrating and nourishing skin, comprising a step of taking up and holding in hand a container comprising a liquid cosmetic according to claim 1, a step of shaking the container with hand so as to allow the capsule to be in a dispersed state in the aqueous medium, a step of pumping the liquid cosmetic out of the container, and a step of applying the cosmetic on skin with hand and rubbing the skin, the method resulting in making the oil component leak out on the skin after breakage of the capsule shell.

\* \* \* \* \*